US00PP25905P2

(12) United States Plant Patent
Smith

(10) Patent No.: US PP25,905 P2
(45) Date of Patent: Sep. 15, 2015

(54) ***CHRYSANTHEMUM* PLANT NAMED 'CIFZ0015'**

(50) Latin Name: *Chrysanthemum×morifolium*
Varietal Denomination: CIFZ0015

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 34 days.

(21) Appl. No.: 13/999,368

(22) Filed: Feb. 18, 2014

(51) Int. Cl.
*A01H 5/02* (2006.01)

(52) U.S. Cl.
USPC ..... Plt./291

(58) Field of Classification Search
USPC ..... Plt./291
CPC ..... A01H 5/0255; A01H 5/025; A01H 5/02
See application file for complete search history.

*Primary Examiner* — Kent L Bell
(74) *Attorney, Agent, or Firm* — Joshua L. Price

(57) ABSTRACT

A new garden type *Chrysanthemum* plant named 'CIFZ0015' particularly distinguished by its light purple colored, small to medium size, decorative-type inflorescences, small to medium plant size with very round, tight and even plant habit , and an early to mid-September natural flowering response.

1 Drawing Sheet

Latin name of the genus and species of the plant claimed: *Chrysanthemum×morifolium.*

Varietal denomination: 'CIFZ0015'.

BACKGROUND OF THE NEW PLANT

The present invention comprises a new *Chrysanthemum*, botanically known as *Chrysanthemum×morifolium*, and hereinafter referred to by the variety name 'CIFZ0015'.

'CIFZ0015' is a product of a planned breeding program. The new cultivar has small to medium size decorative-type inflorescences, small to medium plant size with very round plant habit and a natural season flowering response of early to mid-September.

'CIFZ0015' originates as a natural whole plant mutation of 'Synjac Peafus', U.S. Plant Pat. No. 22,655. 'CIFZ0015' was discovered and selected by the inventor as a single flowering plant within a large population of the parent cultivar grown in pots outdoors in a controlled breeding program in Alva, Fla. in November 2009. The parent cultivar has more two-toned inflorescence color and a larger overall plant size than that of 'Synjac Peafus'.

The first act of asexual reproduction of 'CIFZ0015' was accomplished when vegetative cuttings were propagated from the initial selection in January 2010 in a greenhouse in Alva, Fla.

BRIEF SUMMARY OF INVENTION

Horticultural examination of plants grown from cuttings of the plant initiated in January 2010, and continuing thereafter, has demonstrated that the combination of characteristics as herein disclosed for 'CIFZ0015' are firmly fixed and are retained through successive generations of asexual reproduction.

'CIFZ0015' has not been observed under all possible environmental conditions. The phenotype may vary significantly with variations in environment such as temperature, light intensity and day length.

A Plant Breeder's Right for this cultivar was applied for in Canada on Mar. 8, 2013 (13-7956). 'CIFZ0015' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0015' with colors being as true as possible with an illustration of this type.

Figure 1:
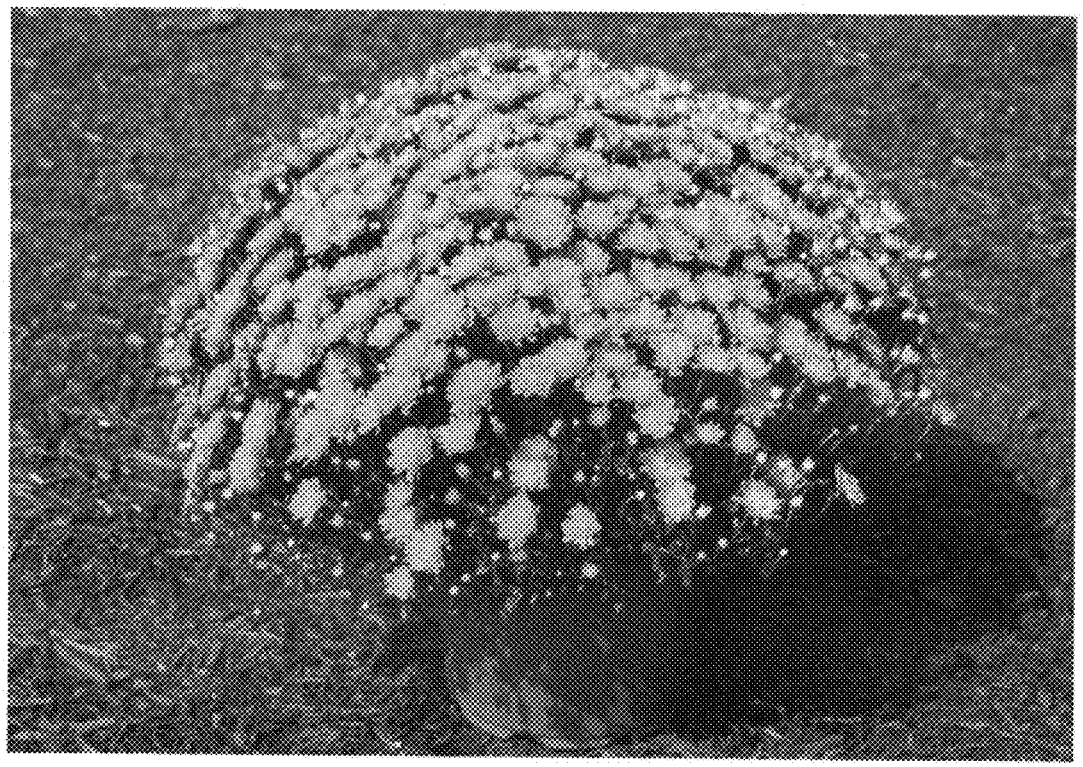
Figure 2:
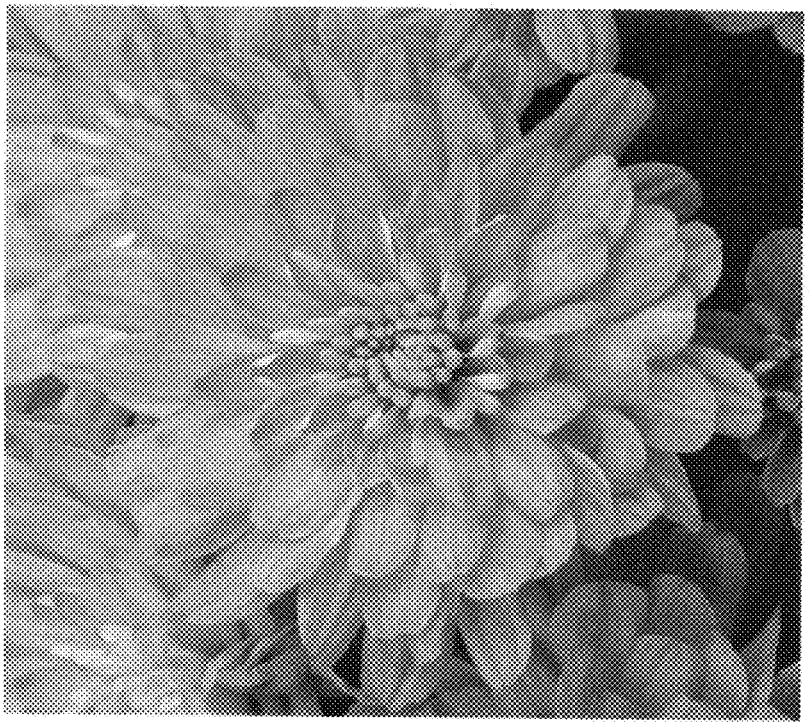

The photographic drawings show in FIG. 1 a flowering plant of the new variety and in FIG. 2 a close-up of the inflorescences.

DETAILED BOTANICAL DESCRIPTION

The plant descriptions and measurements were taken in Gilroy, Calif. in early September 2013 outdoors in natural light. Black-out by black cloth was applied to control day length and to induce early flowering. These plants had been grown in 6 inch pots in a greenhouse trial and were about 11 weeks old. These plants were not pinched.

The aforementioned photographs were taken in September 2012 in Monroeville, N.J. These plants were about 13-14 weeks of age. They were grown one plant per nine inch pot. These plants were not pinched.

Color references are made to The Royal Horticultural Society Colour Chart (R.H.S.) 2001.

TABLE 1

DIFFERENCES BETWEEN THE NEW VARIETY 'CIFZ0015' AND TWO MOST SIMILAR VARIETIES

| | 'CIFZ0015' | 'Synjac Pinka' (U.S. Plant Pat. No. 22,552) |
|---|---|---|
| Flowering response (blackcloth): | ½ week faster | Slower |
| Flowering response (natural): | ½ week faster | Slower |

TABLE 1-continued

DIFFERENCES BETWEEN THE NEW VARIETY 'CIFZ0015' AND TWO MOST SIMILAR VARIETIES

| | | |
|---|---|---|
| Plant size: | Bit smaller | Bit larger |
| Flower color: | Darker shade of lavender | Regular shade of lavender |
| | 'CIFZ0015' | 'Yoursula' (U.S. Plant Pat. No. 13,641) |
| Flowering response (blackcloth): | ½ week slower | Faster |
| Flowering response (natural): | ½ week faster | Slower |
| Plant size: | Larger | Smaller |
| Flower color: | Darker shade of lavender | Regular shade of lavender |

Plant:

*Form, growth and habit.*—Herbaceous garden-type, stems upright and outwardly spreading, freely branching, strong and moderately vigorous growth habit.

*Plant height.*—20-22 cm.

*Plant height (inflorescence included).*—27-30 cm.

*Plant width.*—48-53 cm.

Roots:

*Number of days to initiate roots.*—About 4 days at about 22 degrees C.

*Number of days to produce a rooted cutting.*—4-6 days at 22 degrees C.

*Type.*—Fine, fibrous, free branching.

*Color.*—RHS N155B but whiter.

Foliage:

*Arrangement.*—Alternate.

*Immature leaf, color upper surface.*—RHS 137A.

*Immatrue leaf, color lower surface.*—RHS 137C.

*Mature leaf, color, upper surface.*—RHS 137A.

*Mature leaf, color lower surface.*—RHS 137C.

*Length.*—4.1-4.3 cm.

*Width.*—3.1-3.3 cm.

*Shape.*—Ovate.

*Base shape.*—Attenuate.

*Apex shape.*—Apiculate.

*Margin.*—5-lobed (palmate), edge serrulate.

*Texture, upper surface.*—Bifid hairs.

*Texture, lower surface.*—Bifid hairs.

*Color of veins, upper surface.*—RHS 147B.

*Color of veins, lower surface.*—RHS 147B.

*Pattern of veining.*—Palmate.

*Petiole color.*—RHS 147B.

*Length.*—1.0-1.3 cm.

*Diameter.*—2.0-2.5 cm.

*Texture.*—Covered with bifid hairs.

Stem:

*Quantity of main branches per plant.*—8-10.

*Color of stem.*—RHS 146E.

*Length of stem.*—12-14 cm.

*Diameter.*—0.3 cm.

*Length of internodes.*—0.5-1.0 cm.

*Texture.*—Bifid hairs.

*Color of peduncle.*—From RHS 146A to 146B.

*Length of peduncle.*—7.5-9.0 cm.

*Peduncle diameter.*—0.15 cm.

*Texture.*—Bifid hairs.

Inflorescence:

*Type.*—Compositae, solitary, decorative-type inflorescences borne terminally above foliage, ray florets arranged acropetally on a capitulum.

*Quantity of short days to flowering (response time).*—Approximately 7 weeks.

*Natural season flowering.*—Early to mid-September.

*Quantity of inflorescences per plant.*—80-100.

*Lastingness of individual blooms on the plant.*—About six weeks from first color.

*Fragrance.*—Slightly spicy.

Bud (just when opening/showing color):

*Color.*—Near RHS N155B, soon turning RHS 73A or 73B at the top.

*Length.*—0.8-1.2 cm.

*Width.*—1.0-1.2 cm.

*Shape.*—Oblate (almost globular).

Immature inflorescence:

*Diameter.*—4.2-4.5 cm.

*Color of ray florets, upper surface.*—Ground color RHS 76C, overlain with shades of RHS 72C.

*Color of ray florets, lower surface.*—Close to RHS 76C, near margin RHS N78C.

Mature inflorescence:

*Diameter.*—4.7-4.9 cm.

*Depth.*—1.5 cm.

*Total diameter of disc.*—0.3-0.4 cm.

*Receptacle color.*—RHS 137A.

*Receptacle height.*—0.25-0.30 cm.

*Receptacle diameter.*—0.3 cm.

Ray florets:

*Average quantity of florets.*—Between 50 and 100 in several whorls.

*Color of florets, upper surface.*—From RHS N78B to N78C.

*Color of florets, lower surface.*—RHS 69D with RHS N78B margins.

*Length.*—2.1-2.3 cm.

*Width.*—0.55-0.60 cm.

*Shape.*—Oblong.

*Apex shape.*—Rounded, often slightly praemorse.

*Base shape.*—Attenuate.

*Margin.*—Entire.

*Texture, upper surface.*—Papillate.

*Lower surface.*—Papillate.

Disc florets:

*Average quantity of florets.*—About 15-20.

*Color of florets.*—RHS 1C near base, RHS 13A at apex.

*Length.*—0.35 cm.

*Width.*—0.1 cm.

*Shape.*—Tubular, elongated.

*Apex shape.*—Acute, 5 pointed.

Phyllaries:

*Quantity.*—Approximately 20.

*Color, upper surface.*—RHS 147A.

*Color, lower surface.*—RHS 137A.

*Length.*—In 2 different sizes: 0.4 or 0.8 cm.

*Width.*—0.2-0.3 cm.

*Shape.*—Lanceolate.

*Apex shape.*—Acute.

*Base.*—Fused.

*Margins.*—Entire.

*Texture, upper surface.*—Glabrous.

*Texture, lower surface.*—Bifid hairs.

Reproductive organs:

*Pistil*.—One; is developed both in disc and ray florets.
*Length*.—0.2-0.4 cm.
*Style color*.—RHS 150B.
*Style length*.—0.1 - 0.3 cm.
*Stigma color*.—RHS 13B.
*Stigma shape*.—Bi-parted.
*Ovary color*.—RHS 145C.
*Ovary length*.—0.1 cm.
*Ovary width*.—0.1 cm.
*Stamens*.—4, found on only on the disc florets.
*Color of filaments*.—RHS 150C.
*Length filaments*.—0.2 cm.
*Anther color*.—RHS 14B.
*Anther length*.—0.1 cm.
*Anther shape*.—Oblong.
*Color of pollen*.—RHS 15C.
*Pollen amount*.—Sparse.

Fertility/seed set: Has not been determined to date.
Disease/pest resistance: Has not been determined to date.

What is claimed is:

1. A new and distinct variety of *Chrysanthemum* plant named 'CIFZ0015' substantially as illustrated and described herein.

* * * * *